(12) United States Patent
Gelder et al.

(10) Patent No.: US 9,415,061 B2
(45) Date of Patent: Aug. 16, 2016

(54) COMPOSITIONS AND METHODS FOR TREATMENT OF NEOPLASTIC DISEASE

(75) Inventors: Frank B Gelder, Auckland (NZ); Gillian Alison Webster, Auckland (NZ)

(73) Assignee: Innate Immunotherapeutics Limited, Auckland (NZ)

(*) Notice: Subject to any disclaimer, the term of this patent is extended or adjusted under 35 U.S.C. 154(b) by 559 days.

(21) Appl. No.: 12/935,871

(22) PCT Filed: Apr. 1, 2009

(86) PCT No.: PCT/NZ2009/000049
§ 371 (c)(1),
(2), (4) Date: Mar. 28, 2011

(87) PCT Pub. No.: WO2009/123481
PCT Pub. Date: Oct. 8, 2009

(65) Prior Publication Data
US 2011/0165250 A1  Jul. 7, 2011

(30) Foreign Application Priority Data
Apr. 1, 2008  (NZ) ........................................ 567096

(51) Int. Cl.
*A61K 38/14* (2006.01)
*A61K 31/738* (2006.01)
*A61K 39/00* (2006.01)
*A61K 31/337* (2006.01)
*A61K 47/48* (2006.01)

(52) U.S. Cl.
CPC ............. *A61K 31/738* (2013.01); *A61K 31/337* (2013.01); *A61K 47/4833* (2013.01); *A61K 2039/6062* (2013.01)

(58) Field of Classification Search
CPC ................ A61K 38/14; A61K 31/738; A61K 2039/6062
See application file for complete search history.

(56) References Cited

U.S. PATENT DOCUMENTS

| | | | | |
|---|---|---|---|---|
| 4,177,263 A | * | 12/1979 | Rosenberg et al. | ........... 424/649 |
| 4,357,322 A | * | 11/1982 | Rooks, II | .............. A61K 31/70 514/12.2 |
| 4,397,844 A | * | 8/1983 | Baschang | .............. A61K 39/00 514/20.9 |
| 4,574,058 A | * | 3/1986 | Baschang | .............. A61K 39/00 260/998.2 |
| 4,994,440 A | * | 2/1991 | Creaven | ................. A61K 38/14 514/15.4 |
| 5,208,022 A | * | 5/1993 | Eggers | ............... A61K 39/0011 424/184.1 |
| 5,877,147 A | * | 3/1999 | Pinegin | ................. A61K 38/14 424/117 |
| 5,936,076 A | * | 8/1999 | Higa et al. | .................... 536/17.9 |
| 6,043,347 A | | 3/2000 | Gelder | |
| 6,258,599 B1 | | 7/2001 | Gelder | |
| 6,335,017 B1 | | 1/2002 | Gelder | |
| 6,670,181 B2 | | 12/2003 | Gelder | |
| 2002/0086034 A1 | | 7/2002 | Gelder | |
| 2004/0141996 A1 | | 7/2004 | Gelder | |
| 2005/0191285 A1 | * | 9/2005 | Cheever et al. | ........... 424/93.21 |
| 2007/0154917 A1 | | 7/2007 | Gelder | |

FOREIGN PATENT DOCUMENTS

| | | | |
|---|---|---|---|
| WO | WO 98/15658 A1 | 4/1998 | |
| WO | WO 9815658 A1 | * 4/1998 | |
| WO | WO 2007/120368 | 10/2007 | |
| WO | WO 2008070564 A1 | * 6/2008 | ............. A61K 38/14 |

OTHER PUBLICATIONS

Fidler, Isaiah J. "Macrophages and metastasis—a biological approach to cancer therapy: presidential address." Cancer research 45.10 (1985): 4714-4726.*
Geetha, B., and A. J. I. T. Sodhi. "Effect of cisplatin, lipopolysaccharide, muramyl dipeptide and recombinant interferon-gamma on murine macrophages in vitro. I. Macrophage-mediated tumor cell lysis." Natural immunity and cell growth regulation 8.2 (1989): 100 (PubMed Abstract No. 2503714).*
Merriam-Webster.com. 2014. http://merriam-webster.com/dictionary/diffusion (accessed Feb. 4, 2014).*
Remington, Joseph Price. Remington: The science and practice of pharmacy. Eds. David B. Troy, and Paul Beringer. vol. 1. Lippincott Williams & Wilkins, 2006, p. 955.*
CAS Registry No. 53678-77-6 (Nov. 16, 1984).*
Rudt, S., and R. H. Müller. "In vitro phagocytosis assay of nano-and microparticles by chemiluminescence. I. Effect of analytical parameters, particle size and particle concentration." Journal of controlled release 22.3 (1992): 263-271.*
Morin, C., et al., "Biodegradable Nanocapsules Containing a Lipophilic Immunomodulator: Drug Retention and Tolerance Towards Macrophage In Vitro", Journal of Drug Targeting, 1993, 1:157-164.
Tabata, Y., et al., "Macrophage activation through phagocytosis of muramyl dipeptide encapsulated in gelatin microspheres", Journal of Pharmacy and Pharmacology, 1987, 39:698-704.
International Search Report for International Application PCT/NZ2009/000049, dated Jul. 22, 2009.
Azuma, et al., "Development of immunoadjuvants for immunotherapy of cancer", International Immunopharmacology, 1:1249-1259(2001).
Uehara, et al., *The Japan Society for Clinical Immunology*, 45(3): 275-280(2006).
Tabata, et al., "Activation of Macrophage in vitro to Aquire Antitumor Activity by a Muramyl Dipeptide Derivative Encapsulated in Microspheres Composed of Lactide Copolymer", *Journal of Controlled Release*, 6:189-204(1987).
Barratt, et al., "Anti-Metastatic Activity of MDP-L-Alanyl-Cholesterol Incorporated Into Various Types of Nanocapsuies", International Society for Immunopharmacology, 16(5/6): 457-461(1994).
Merhi, et al., "Synthesis and Immunostimulating Properties of Lipophilic Ester and Ether Myramyl Peptide Derivatives", J. Med. Chem, 39:4483-4488(1996).
Makino, et al., "Phagocytic uptake of polystyrene microspheres by alveolar macrophages: effects of the size and surface properties of the microspheres", Colloids and Surfaces, 27:33-39(2003).
Champion, et al., "Role of Particle Size in Phagocytosis of Polymeric Microspheres", Pharm Res., 25(8):1815-1821(2008).

* cited by examiner

*Primary Examiner* — Bethany Barham
*Assistant Examiner* — Peter Anthopolos
(74) *Attorney, Agent, or Firm* — Lisa M. Warren, Esq.; Morse, Barnes-Brown & Pendleton, P.C.

(57) ABSTRACT

The present invention is concerned with immunostimulant compositions, in particular compositions comprising microparticulate form of murmyl dipeptide, and their use in the treatment of neoplastic disease.

20 Claims, 13 Drawing Sheets

(A)

(B)

* denotes statistical significance relative to control (P≤0.0006; unpaired one-tailed t-test)
* denotes significance relative to each individual therapy (P < 0.0001)

(A)

(B)

COMPOSITIONS AND METHODS FOR TREATMENT OF NEOPLASTIC DISEASE

CROSS-REFERENCE TO RELATED APPLICATIONS

This application is a national stage filing under 35 U.S.C. 371 of International Application PCT/NZ2009/000049, filed Apr. 1, 2009, which claims priority to New Zealand Application No. 567096, filed on Apr. 1, 2008. International Application PCT/NZ2009/000049 was published under PCT Article 21(2) in English.

FIELD OF THE INVENTION

The present invention relates generally to an immunostimulant and in particular, to the use of an immunostimulant in the form of a muramyl dipeptide microparticle in the treatment of neoplastic disease.

The invention has been developed primarily for use as a treatment for neoplastic disease and will be described hereinafter with reference to this application. However, it will be appreciated that the invention is not limited to this particular field of use.

BACKGROUND OF THE INVENTION

Any discussion of the prior art throughout the specification should in no way be considered as an admission that such prior art is widely known or forms part of common general knowledge in the field.

Neoplastic disease or cancer is a group of diseases in which genetically abnormal cells tend to proliferate in an uncontrolled manner and may metastasise. Nearly all cancers are caused by abnormalities in the genetic material of the transformed cells. These abnormalities may be due to the effects of carcinogens such as tobacco smoke, ionising radiation, chemicals or infectious agents. Other cancer promoting genetic abnormalities may be randomly acquired through errors in DNA replication, or are inherited and are present in all cells from birth.

Current treatment regimes for cancer include one or more of surgery, chemotherapy, radiation therapy, immunotherapy, monoclonal antibody therapy or other methods. The choice of therapy depends upon the location and grade of the tumour and the stage of the disease, as well as the general health of the patient.

The ultimate aim of the aforementioned treatment regimes is the complete removal of the cancer without damage to the rest of the body. Sometimes this can be accomplished by surgery, but the propensity of cancers to invade adjacent tissue or to spread to distant sites by microscopic metastasis often limits its effectiveness. Chemotherapy is often limited by toxicity to other tissues in the body and radiation therapy can also cause damage to normal tissue.

The potentiation of innate anti tumour mechanisms by immunostimulatory compounds is a clinically relevant therapeutic approach to treating neoplastic disease. While NK and LAK cells play a central role in tumour cell surveillance and destruction, other innate immune cell subsets such as NKTs, monocytes/macrophages and dendritic cell subsets represent additional non-redundant arms of innate anti-tumour responses. Together these cell subsets are known to kill tumour targets by several mechanisms including granule-associated granzyme and perforin mediated killing as well as secretory mechanisms such as FasL, TRAIL and tumour necrosis factor-alpha (TNFα)-mediated pathways.

The potentiation of such cell subsets by an immunostimulant would provide an effective mono- or co-therapy for use in the treatment of neoplastic disease that is non-invasive and substantially less toxic than current treatment regimes.

Previously, applicant has disclosed an immunostimulant in the form of a muramyl dipeptide microparticle for the treatment of HIV and Anthrax in Australian Patent No. 732809 and New Zealand Patent Application No. 555582, respectively. However, Applicant has surprisingly and unexpectedly found that a muramyl dipeptide microparticle is useful in the treatment of neoplastic disease.

It is an object of the present invention to overcome or ameliorate at least one of the disadvantages of the prior art, or to provide a useful alternative.

SUMMARY OF THE INVENTION

The present invention is in part based on a surprising observation that a muramyl dipeptide cross-linked into a microparticle (MDP-microparticle) contains immunostimulatory nucleic acid motifs, which may explain why it was also observed, as described herein, that the MDP-microparticle is capable of activating several different immune cell subsets that are central to induction of a broad range of innate anti-neoplastic immune responses. Hereinafter the MDP-microparticle that comprises the nucleic acid motifs will be referred to as "MDP/DNA-microparticle".

Further, the MDP/DNA-microparticle may be functionalised with one or more additional ligands capable of enhancing innate anti-neoplastic immune responses.

Thus, according to a first aspect the present invention provides a method of treating neoplastic disease comprising the administration to a subject requiring such treatment of an effective amount of an MDP/DNA-microparticle.

To enhance the efficacy of the innate anti-neoplastic immune response the MDP/DNA-microparticle may be combined with at least one immunostimulatory ligand, bound to or co-administered within the microparticle, that is capable of stimulating specific immune cell which are effective in mediating tumour cell damage and/or destruction. Suitable ligands may be selected from known ligands of described pathogen molecular pattern recognition receptors including TLR1,2,3, 4,5,6,7,8,9,10, NOD-1, NOD-2 and the like. Other useful innate immunostimulatory receptors are well known in the art and can be easily identified by those skilled in the art.

Preferably, the immunostimulatory ligands are cross-linked on the surface or within the MDP/DNA-microparticle.

Preferably, the MDP/DNA-microparticle per se has an overlapping immunostimulatory profile with interleukin-2 (IL-2). This is advantageous, as IL-2 has been demonstrated to have clinical activity against renal cell carcinoma, bladder carcinoma, melanoma, lymphoma and some leukaemias. This is advantageous as the MDP/DNA-microparticle may be used in adjunctive therapy with less toxic doses of IL-2 in the treatment of a neoplastic disease.

It is an advantage that the MDP/DNA-microparticle also stimulates the production of anti-neoplastic cytokines such as interferon-gamma (IFNγ), IL-12, IFN-α and TNFα.

It is a further advantage that the MDP/DNA-microparticle stimulates the production of cytokines and growth factors that support immune cell replenishment and functional reconstitution such as GM-CSF, IL-7 and IL-3. This is advantageous when the MDP/DNA-microparticle is used as an adjunct to radiotherapy or chemotherapy to counteract the myelosuppression and leukopenia associated with such anti-neoplastic therapies.

Preferably, the MDP/DNA-microparticle has adjuvant properties which induce antigen processing and presentation leading to the generation of Th1-type cellular anti-tumour immunity in the presence of tumour antigen. This is of further advantage when the MDP/DNA-microparticle is used as an adjunct to therapies that cause autologous tumour antigen release such as local tumour irradiation and chemotherapy.

The compositions of the present invention may be used in the treatment of primary tumours, such as for example breast, prostate, colon, bladder, lung, skin (melanoma). However, the compositions of the present invention are particularly effective in the treatment of metastases (metastatic disease) that may arise from primary tumours. In that regard, the nature or origin of the primary tumour is not of importance with respect to efficacy of the MDP/DNA-microparticle compositions.

Thus, the neoplastic disease may be selected from the group consisting of carcinoma, sarcoma, myeloma, leukaemia, lymphoma or a mixed-type. Most preferably, the neoplastic disease is selected from fibrosarcoma, myxosarcoma, liposarcoma, chondrosarcoma, osteosarcoma, chordoma, malignant fibrous histiocytoma, hemangiosarcoma, angiosarcoma, lymphangiosarcoma, mesothelioma, acute myelogenous leukaemia, acute lymphoblastic leukaemia, chronic myelogenous leukaemia, chronic lymphoblastic leukaemia, plasmacytoma, multiple myeloma, Hodgkin lymphoma and non-Hodgkin lymphoma, rhabdomyosarcoma, leiomyosarcoma, squamous cell carcinoma, epidermoid carcinoma, adenocarcinoma, hepatocellular carcinoma, renal cell carcinoma, hypernephroma, cholangiocarcinoma, transitional cell carcinoma, choriocarcinoma, seminoma, embryonal cell carcinoma, glioma, anaplastic glioblastoma multiforme, neuroblastoma, medulloblastoma, malignant meningioma, malignant meningioma, malignant schwannoma, neurofibrosarcoma, parathyroid carcinoma, medullary carcinoma of thyroid, bronchial carcinoid, oat cell carcinoma, malignant pheochromocytoma, islet cell carcinoma, malignant carcinoid, malignant paraganglioma, melanoma, malignant schwannoma, merkel cell neoplasm, cystosarcoma phylloides, Wilms' tumour, dysgerminoma, retinoblastoma and teratocarcinoma.

Advantageously, the MDP/DNA-microparticle may be used as a co-therapy in combination with one or more other anti-neoplastic agents for the treatment of neoplastic disease. In this form of therapy the MDP/DNA-microparticle may also be functionalised on its surface with one or more immunostimulatory ligands. Preferably, the one or more other anti-neoplastic agents are selected from alkylating agents, for example, cisplatin, carboplatin, busulfan, chlorambucil and carmustine; antimetabolites, for example, azathioprine and mercaptopurine; alkaloids, for example, vincristine, vinblastine, vinorelbine, vindesine, podophyllotoxin and taxol; type I or type II topoisomerase inhibitors; antibiotics, for example, dactinomycin, bleomycin and doxorubicin or hormones and cytokines, for example, IL-2, IFNγ, GM-CSF, IL-12 or IFN.

Alternatively, the one or more other anti-neoplastic agents may be used in adjunctive therapy with the MDP/DNA-microparticle (with or without bound immunostimulatory ligands on its surface). Such therapy may include administration of the anti-neoplastic agent and the MDP/DNA-microparticle simultaneously with or sequentially. Sequential administration may be separated by any suitable time-frame of minutes, hours, days or weeks.

It will be appreciated that the above list of anti-neoplastic agents is not exhaustive and that other anti-neoplastic agents can be used as a co-therapy together with the MDP/DNA-microparticle or with the MDP/DNA-microparticle bound to one or more immunostimulatory ligands.

It will be further appreciated that the MDP/DNA-microparticle will be formulated with a pharmaceutically acceptable carrier. Suitable carriers and formulations will be known to those of skill in the art or obtainable from, for example, the British Pharmacopoeia, Remington's, and the like.

Preferably, the MDP/DNA-microparticle is resistant to treatment with pepsin and extremes of pH and denaturing conditions. In particular, the MDP/DNA-microparticle is resistant to a) treatment with pepsin at pH 3.5, b) a pH of less than 1 and greater than 11 at ambient temperature, c) denaturing conditions in 6 M urea or 6 M guanidine hydrochloride and d) nuclease (DNAse) activity While not wishing to be bound by any particular theory as to how the present invention works, Applicant believes that the ability of the MDP/DNA-microparticle to treat a broad spectrum of tumours arises from the demonstrable activation of natural killer cells (NK) and natural killer T cells (NKT) as a consequence of MDP/DNA-microparticle mediated activation of myeloid and plasmacytoid dendritic cells and the induction of subsequent natural killer cell NK/NKT/dendritic cell cross-talk through up-regulation of cytokine production and receptor modulation. This is advantageous as NK and NKT cells have been shown to play a role in controlling metastatic spread of certain neoplastic diseases following surgical removal of a solid tumour.

Accordingly, in a second aspect, the present invention provides a method of treating metastases (metastatic disease) in a subject having a neoplastic disease comprising the administration to the subject requiring such treatment of an effective amount of an MDP/DNA-microparticle.

This is advantageous as metastatic disease can occur spontaneously or following surgical removal of a tumour.

According to a third aspect, the present invention provides a method of modulating tumour recognition receptors and/or tumour immunogenicity in a subject having a neoplastic disease comprising the administration to the subject requiring such treatment of an effective amount of an MDP/DNA-microparticle.

Preferably, the MDP/DNA-microparticle modulates tumour recognition receptors and/or tumour immunogenicity by up-regulation of MHC class I molecules and non-MHC antigens on tumour cells.

Advantageously, the MDP/DNA-microparticle in accordance with the present invention has been shown to be a potent non-toxic vaccine adjuvant.

Accordingly, the present invention provides, in a fifth aspect, a method for enhancing efficacy of an anti-tumour vaccine administered to a subject having a neoplastic disease comprising the administration to said subject of said vaccine and an effective amount of an MDP/DNA-microparticle.

It will be understood that the vaccine and the MDP/DNA-microparticle may be administered to the subject simultaneously or sequentially.

Preferably, one or more ligands capable of enhancing the anti-neoplastic response may be covalently attached to the MDP/DNA-microparticle.

According to a sixth aspect the present invention provides a method of potentiating NK and/or NKT cell activity in a subject having a neoplastic disease, comprising the administration to a subject requiring such treatment of an effective amount of an MDP/DNA-microparticle.

The MDP/DNA-microparticle may potentiate NK and/or NKT cells directly or indirectly.

According to a seventh aspect the present invention provides a method of stimulating release of cytokines, chemokines, hematopoietic and myelorestorative factors and cytotoxic proteins in a subject having a neoplastic disease comprising the administration to a subject requiring such treatment of an effective amount of an MDP/DNA-microparticle.

Preferably, the cytokines, chemokines and cytotoxic proteins are selected from IL-2, IFNγ, IFNα, GM-CSF, IL-3, IL-7, IL-12p70, TRAIL, TNFα and/or FasL.

Preferably, the MDP/DNA-microparticle stimulates secretion of IFNα from peripheral blood plasmocytoid dendritic cells (pDCs).

Preferably, the MDP/DNA-microparticle stimulates secretion of TNFα from macrophages/monocytes.

Preferably the MDP/DNA-microparticle stimulates secretion of IFNγ from NK cells

Preferably the MDP/DNA-microparticle is administered intravenously. Alternatively, the MDP/DNA-microparticle may be administered by other routes, for example orally, intraperitoneally, intramuscularly and the like.

It will be appreciated that suitable tumour-specific antigens may also be bound to the MDP/DNA-microparticle, in order to stimulate a tumour specific immune response, thus being useful as a vaccine. Suitable antigens may be selected from autologus tumour cells or from prior art known antigens, such as CEA, CA19-9, CA125, EP-CAM, her-2/neu, melanoma antigen, GM2 and the like.

According to an eighth aspect the present invention provides use of a muramyl dipeptide cross-linked into a microparticle for the manufacture of a medicament for the treatment of neoplastic disease or metastatic disease.

In the context of the present invention a reference to "muramyl dipeptide microparticle" may be used interchangeably with "MDP/DNA-microparticle" and "MIS-416". In the figures the terms "MIS" or "MIS 416" may be used interchangeably to define the MDP/DNA-microparticle.

The term "anti-neoplastic" as used herein is intended to encompass both destruction/killing of neoplastic cells as well as preventing their growth and/or replication. Thus the activity of the compositions of the present invention may be tumoricidal or tumoristatic in nature.

The terms "neoplastic", "neoplasia" or "neoplastic disease" is intended to describe tumours, both solid and fluid (eg. leukaemias), and includes metastases (metastatic disease) that may arise from such tumours.

BRIEF DESCRIPTION OF THE DRAWINGS

A preferred embodiment of the invention will be described, by way of example only, with reference to the accompanying drawings, in which.

DESCRIPTION OF THE PREFERRED EMBODIMENT

Figure 1:
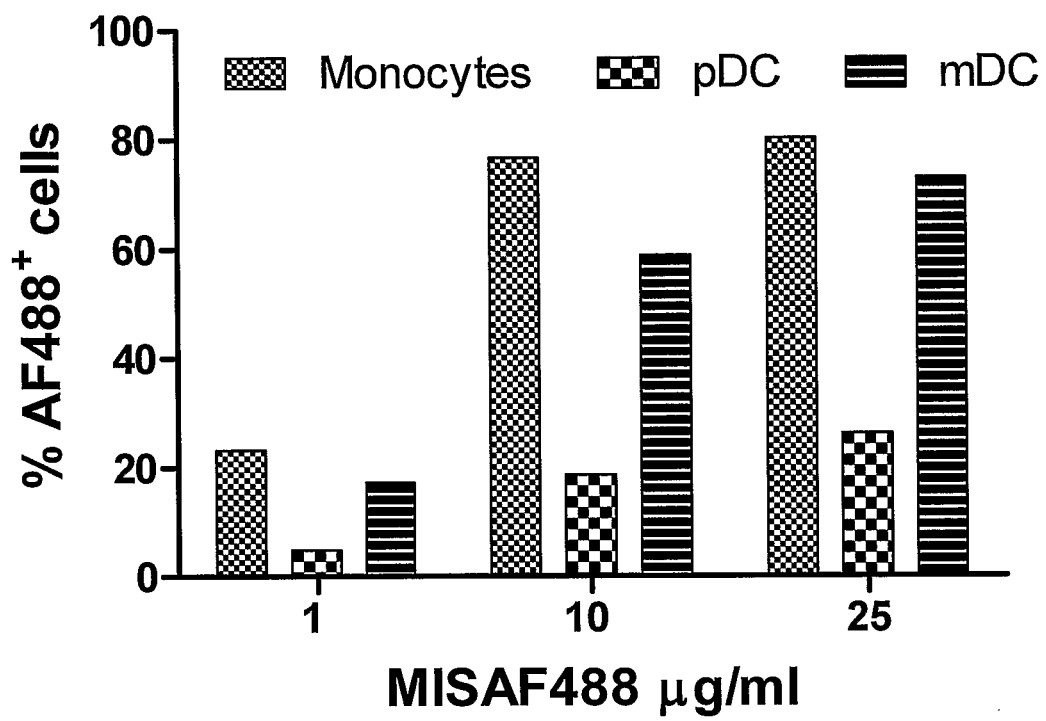
FIG. 1 is a graphical illustration of internalisation of fluorescently labelled MDP/DNA-microparticle (MIS) by peripheral blood monocytes, plasmocytoid and myeloid dendritic cells.

The inventive concept described herein is based in part on the surprising observation that a muramyl dipeptide cross-linked into a microparticle (MDP-microparticle) contains DNA fragments, probably of bacterial origin, which may explain a further surprising observation that the microparticle is capable of selectively targeting and activating several different immune cell subsets that are central to induction of a broad range of innate and adaptive anti-neoplastic immune responses. This novel MDP-microparticle comprising DNA fragment(s) will be referred to herein as "MDP/DNA-microparticle".

Whereas the MDP/DNA-microparticle compositions of the present invention are themselves effective in targeting and activating the relevant components of the immune system to aid in destructions of neoplastic cells, the efficacy of the microparticle compositions can be further enhanced and focused by certain ligands that can be coupled to the surface of the microparticles.

The activation of innate anti-tumour mechanisms by immunostimulatory compounds is now well established as a therapeutic approach for the treatment of cancer. Whilst natural killer (NK) cells play a central role in tumor cell immunosurveillance and destruction, NKT, myeloid and plasmocytoid dendtritic cells as well as monocyte/macrophages represent additional non-redundant arms of innate anti-tumor immunity Together these subsets kill tumor targets by several mechanisms which include granzyme, perforin, Fas-FasL, TRAIL and TNF-α. As well as having direct anti-tumour activity, these cell subsets also underpin the adaptive immune response, which may lead to the development of autologous tumour-specific immunity in the presence of exogenous or endogenous tumour antigen. Another feature associated with particular immunostimulants is their potential to trigger a range of innate and adaptive anti-tumour mechanisms as well as reconstitute the immune system following the deleterious effects of irradiation and chemotherapy. The importance of the adaptive wing of the immune system in containing tumor growth is supported by animal studies and various observations in humans. These include increased prevalence of certain tumors following immunosuppression as well as the demonstration, that the presence of intralesional T cells is correlated with improved clinical outcome in various solid tumors. In particular in colon carcinoma, the presence of CD8+ T cells within the tumor microenvironment was significantly associated with a better survival in several studies. T cell responses against specific tumor-associated antigens (TAA) are frequently detected in the peripheral blood of tumor patients of various histiotypes including colorectal cancer, melanoma, acute myeloid leukemia, breast cancer, neuroblastoma, and head and neck cancer. Data from selected single patients suggest a favorable clinical course in patients with peripheral, spontaneous TAA-directed T cells. TAA-directed T cell responses can reliably be induced using various vaccination approaches. Several recent reports have found a correlation between induction of a TAA-directed T cell response by vaccination and clinical response. Preliminary data also suggest a possibly favorable clinical effect of vaccine-induced T cells in adjuvant vaccination.

Spontaneous T cell responses against TAAs including CEA, Ep-CAM, or her-2/neu have been demonstrated in peripheral blood of approximately 25% of colorectal cancer patients. These cells were identified in functional T cell assays by antigen-induced IFNγ production. More detailed analyses in some samples revealed a CD3+CD8+IFNγ+CD69+CD45RA+ phenotype, indicative of an effector T cell subset that is able to directly mediate tumor cell lysis. Spontaneous TAA-specific T cells with the potential of effector cells should be capable of destroying tumor cells and thereby lead to elimination of residual disease or prevent tumor progression.

In one embodiment the present invention contemplates use of the MDP/DNA-microparticles in conjunction with one or more TAAs which are likely to elicit protective immune responses in a mammal, in the form of a vaccine for treating or preventing cancers. The TAA may be co-administered with the MDP/DNA-microparticle, in which case it is preferred that the TAA is conjugated to the surface of the microparticle, or it may be administered sequentially in any order.

The MDP/DNA-microparticle compositions of the present invention can deliver cancer vaccine candidates including autologus tumor vaccines, and vaccines comprised of CEA, CA19-9, CA125, EP-CAM, her-2/neu, melanoma antigen GM2, thereby permitting prophylaxis against and treatment of a variety of neoplastic diseases. In addition, the MDP/DNA-microparticle compositions of the present invention can be used to treat an already existing neoplastic disease or to accompany conventional cancer treatments. The compositions of the present invention can completely or partly avoid the considerable disadvantages associated with conventional cancer treatments.

Some of the advantageous physico-chemical properties of the MDP/DNA-microparticle of the present invention are resistance to treatment with pepsin and extremes of pH and denaturing conditions. In particular, the MDP/DNA-microparticle is resistant to a) treatment with pepsin at pH 3.5, b) a pH of less than 1 and greater than 11 at ambient temperature and c) denaturing conditions in 6 M urea or 6 M guanidine hydrochloride While not wishing to be bound by any particular theory as to how the present invention works, Applicant believes that the ability of the MDP/DNA-microparticle to treat a broad spectrum of tumours arises from the demonstrable activation of natural killer cells (NK) and natural killer T cells (NKT) mediated by the establishment of myeloid and plasmacytoid dendritic cells crosstalk and up-regulation of cytokine production and receptor modulation. This in turn is thought to be mediated by the particular structure and composition of the microparticle, more particularly the presence of bacterial deoxyribonucleic acid within the structure of the microparticle. Such stimulatory activity is advantageous as NK and NKT cells have been shown to play a role in controlling metastatic spread of certain neoplastic diseases following surgical removal of a solid tumour.

The invention will now be more particularly described with reference to non-limiting examples. The in vitro and in vivo models used herein to demonstrate the invention are selected on the basis of their accepted ability to show anti-neoplastic activity of tested compositions.

EXAMPLES

Example 1

Preparation of MDP/DNA-Microparticle

A multiple repeat of muramyl dipeptide (MDP) isolated from *Propionibacterium acini*, formed the core structure of the MDP/DNA-microparticle carrier complex of this example. The chemical composition of the preferred monomeric subunit is as shown below.

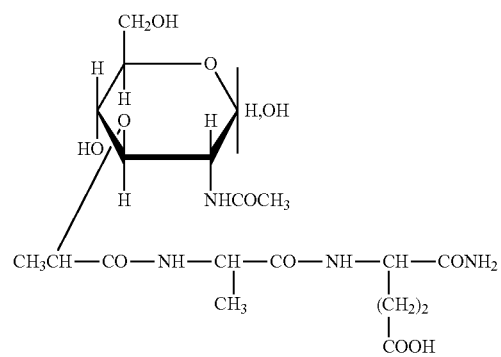

MDP has well known immunostimulatory properties, which have been extensively evaluated in studies designed to determine its effect on increasing immune function. To date, both MDP isolated from natural sources and synthetic MDP have been associated with significant toxicity when administered to mammals. This toxicity has limited the effectiveness of MDP as an adjuvant.

A method for the isolation of MDP and associated bacterial DNA fragments, free from toxic components, is provided herein. *Propionibacterium acnes* was grown to a mid-stationary growth phase and washed to remove contaminants of bacterial culture origin employing techniques well known to those in the art. Hydrophobic components contained in the cell walls and cytoplasm were sequentially extracted by successive washes with increasing concentrations of ethanol/isopropanol/water (10%:10%:80%, 25%:25%:50% and 40%:40%:20%) at elevated temperatures. The isopropyl alcohol is then removed with successive washes with decreasing concentrations (80%, 50%, 40% and 20%) of ethanol at elevated temperatures. The resulting MDP/DNA-microparticle is then suspended in 6M guanidine-HCL and then washed into water for irrigation and its concentration measured by relating its absorbance at 540 nm to the absorbance of turbidity standards. The concentration of the MDP/DNA-microparticle was adjusted to 10 mg/mL for storage and later use.

Analysis of this preparation demonstrated muramyl dipeptide extensively crosslinked with bacterial DNA in a microparticle size predominantly in the range of 1 to 3 microns. The MDP/DNA-microparticles contain muramic acid with amino-linked L-alanine-D-isoglutamine dipeptide and bacterial DNA fragments as the bioactive component. Such a microparticle can be isolated from natural sources, as above, or synthesized using well-known synthetic procedures (for example, Liu G.; Zhang S.-D.; Xia S.-Q.; Ding Z.-K. Bioorganic and Medicinal Chemistry Letters, 10 (12), 2000, pp. 1361-1363(3); Schwartzman S. M., Ribi E., Prep Biochem. 1980; 10(3): 255-67; Ohya et al. Journal of Bioactive and Compatible Polymers, 1993; 8: 351-364). The MDP/DNA-microparticles generated by the present methods can have a broad range of sizes (for example, 0.011-30 microns) but the preferred size is in the range of 0.5-3 microns.

Example 2

Covalent Attachment of Ligands and Immunogens to the MDP/DNA-Microparticle

The attachment of ligands and immunogens to MDP/DNA-microparticle can be accomplished employing reductive amination. Those skilled in the art will recognize that stable carbonyl groups can be produced on MDP/DNA-microparticle, carbohydrate containing ligands/immunogens or on a dextran, polyethelene glycol or mannin bridge by oxidation of carbohydrate with sodium metaperiodate. This results in the formation of stable carbonyl groups (aldehyde) which in turn react spontaneously with amino groups present on certain TLR ligands and immunogens to form Schiff's base intermediates. The addition of sodium cyanoborohydride to a reaction in which Schiff's base formation has occurred results in complete reduction of the labile Schiff's base intermediate to a chemically stable bond (see figure below). Unlike sodium borohydride, sodium cyanoborohydride is sufficiently mild to avoid adversely reducing aldehydes to non reactive hydroxyls. This methodological approach is described in Current Protocols In Immunology; Series Editor: Richard Coico (Cornell University) Published by John Wiley & Sons, Inc.

An example of the method employed is as follows: MDP/DNA-microparticle (20 mg) in 20% ethanol is pelleted by centrifugation, resuspended in and extensively washed with water. The MDP/DNA-microparticle is then pelleted and resuspended at a concentration of 50 mg of the MDP/DNA-microparticle/mL in sodium metaperiodate (0.05-0.5M) and an oxidation reaction is carried out for 1 hour at room temperature. Following activation with sodium metaperiodate, the MDP/DNA-microparticle suspension is pelleted by centrifugation, resuspended in and extensively washed with water. The concentration of the sodium metaperiodate and the reaction time can be varied to regulate the number of activated sites produced within the MDP/DNA-microparticle, ligand, immunogen or the like during oxidation. An activated MDP/DNA-microparticle should react with and covalently attach at least one molecule of the subject immunogen or ligand per MDP/DNA-microparticle, preferably 10-100 molecules of subject peptide or ligand per MDP/DNA-microparticle and most preferably 100 to 1000 subject peptide or ligand per MDP/DNA-microparticle. For a highly activated MDP/DNA-microparticle preparation a final concentration of 0.5 M sodium metaperiodate is used and the oxidation reaction is carried out for one hour. A preferred concentration of sodium metaperiodae is between 5 and 30 mM.

Following sodium metaperiodate oxidation the MDP/DNA-microparticle is then pelleted and washed extensively to removal the sodium metaperiodate. The activated MDP/DNA-microparticle is then re-suspended in the desired immunogen or ligand (for example TLR9 or NOD2 at ≥1 mg/mL at a 20:1 w/w ratio) in sodium bicarbonate buffer (0.1 M pH 9.5) and incubated (ambient temperature) for 18-24 hours. The reactants are centrifuged and the pellet that now contains the immunogen/ligand linked to the MDP/DNA-microparticle through an intermediate Schiff's base is reduced forming a stable covalent linkage between the MDP/DNA-microparticle and the immunogens/ligands. Numerous reducing agents can be employed and sodium borohydride is an example of a reducing agent typically used for this purpose. Following reduction of the Schiff's base the MDP/DNA-microparticle-immunogen/ligand conjugate is pelleted, washed and resuspended in the desired vaccine buffer at the desired immunogen/ligand concentration.

The covalent attachment of immunogen or ligand, if used, to the MDP-DNA microparticle can also be made through bi-functional cross linkers.

Homobifunctional Imidoester Cross-linker-mediated Coupling.

DMA, DMP and DMS (shown below) are water soluble, membrane permeable, homobifunctional imidoester cross-linkers. The imidoester functional group is one of the most specific acylating groups available for the modification of primary amines and has minimal cross reactivity toward other nucleophilic groups in proteins/ligands. In addition, the imidoamide reaction product does not alter the overall charge of the protein, potentially retaining the native conformation and activity of the protein/ligand. Conjugation of protein/ligand is achieved through a two step reaction where MDP/DNA-microparticle is first incubated with the desired imidoester crosslinker chosen from the three shown below based on spacer arm length required to avoid steric hinderance.

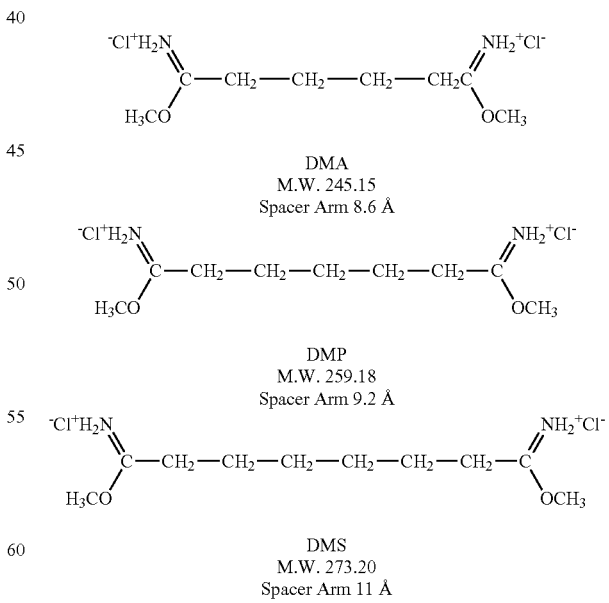

DMA
M.W. 245.15
Spacer Arm 8.6 Å

DMP
M.W. 259.18
Spacer Arm 9.2 Å

DMS
M.W. 273.20
Spacer Arm 11 Å

The free amino groups present on MDP/DNA-microparticle are first saturated by incubation with a 20 fold molar excess of the cross-linker dissolved in 0.2 M triethanolamine, pH 8.0 (reaction buffer). The reaction mixture is incubated at room temperature for 30 minutes and excess crosslinker is removed from the activated MDP/DNA-microparticle by centrifugation and washing (3×) with reaction buffer. Activated MDP/DNA-microparticle is resuspended in reaction buffer containing the desired ligand. The reaction mixture is incubated at room temperature for 1-2 hours and MDP/DNA-microparticle-ligand conjugate is pelleted, washed (×3) with saline glycine buffer (0.05 M glycine pH 6.5, NaCl 0.9%) and bioactivity is measured by cytokine induction assays. Similar proportions of microparticle and immunogen/ligand are used as outlined above for reductive animation attachment method.

It should be noted, although without limitation to the mechanism of action, that the MDP/DNA-microparticle-immunogen/ligand composition likely affects immunogenicity by influencing preferential cell uptake, protein half-life, and antigen presentation through MHC immunological events. When immunization with more than one subject immunogen/ligand is desired, a cocktail of subject immunogen/ligand MDP/DNA-microparticle conjugates can be prepared by mixing individual conjugates at ratios to optimize immunogenicity of each subject peptide introduced in the cocktail. In this configuration sufficient immunogen is available on each microparticle conjugate (100-1000 immunogens-ligands/microparticle) to enhance antigen presentation by a single antigen-presenting/responder cell. Immunogenicity/activity of the subject immunogen/ligand can be optimized by adjusting both the number of subject peptides per MDP/DNA-microparticle carrier and when desired the ratio of immunogens within a vaccine cocktail to achieve the desired immune response. In this configuration, antigen processing by the antigen presenting cell results in a high density, usually more than 100 and most frequently more than 500 peptides, presented at the cell surface of the antigen-presenting cell through MHC interactions.

Other methods for attachment may employ maleimide conjugation chemistries. Maleimide linkage may be performed using a sulfo modified sulfosuccinimidyl-4-cyclohexane-1-carboxylate according to standard protocols using sulfo-SMCC (Pierce) or other linkers suitable for sulfhydryl linkage.

Example 3

Internalisation of Fluorescently Labelled MDP/DNA-Microparticle (MIS) by Peripheral Blood Monocytes, Plasmocytoid (pDC) and Myeloid (mDC) Dendritic Cells Whole blood was incubated with 50, 25, 10 or 1 µg/mL of AlexaFluor 488 (Invitrogen) labelled-MDP/DNA-microparticle (made in house using standard protocol supplied with reagent) and incubated for 30 minutes at 37° C. Flow cytrometric analysis of monocytes, plasmocytoid and myeloid DC was performed following cell labelling with a panel of fluorescent antibodies (Becton Dickinson). Cells were gated based on CD45, BDCA-1, BDCA-2, lineage marker and CD14 expression. The % of each subset that internalised AF488-MDP/DNA-microparticle (MIS) is shown in FIG. 1.

Example 4

MDP/DNA-Microparticle (MIS) Stimulation of Human PBMC Results in the Production of Anti-Neoplastic Cytokines IFN-α, TNF-α and IL-12p70

Figure 2:
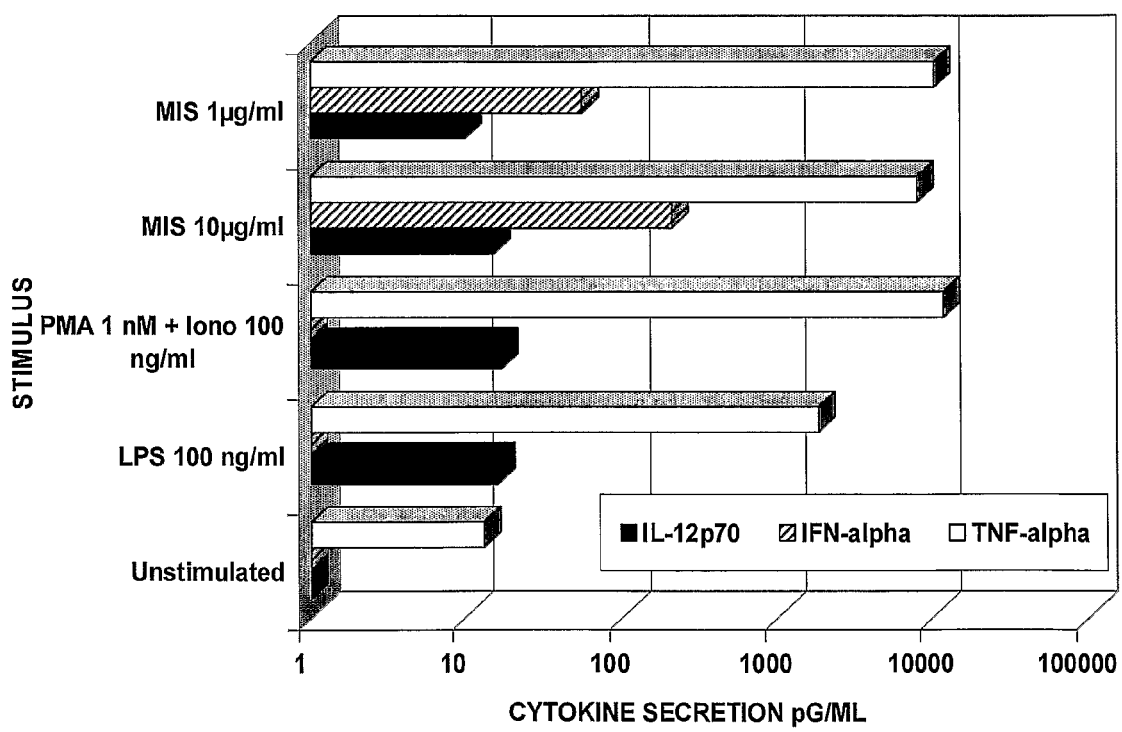
FIG. 2 shows the secretion of anti-neoplastic cytokines IFNα, TNFα and IL-12p70 by MDP/DNA-microparticle (MIS) stimulated human peripheral blood mononuclear cells.

Human PBMC ($10^6$/mL) were cultured with LPS (E coli; 100 ng/mL), PMA (1 nM)+Ionomycin (100 ng/mL) (both assay negative controls for IFN-α production) or MDP/DNA-microparticle (10 and 1 µg/mL) for 96 hours. Supernatants were assayed for secreted IFN-α using flow cytometric cytokine bead array technology according to the manufacturers' standard protocols (Bender MedSystems). FIG. 2 shows that MDP/DNA-microparticle induces IFN-α in a dose-responsive manner.

Example 5

Figure 3:
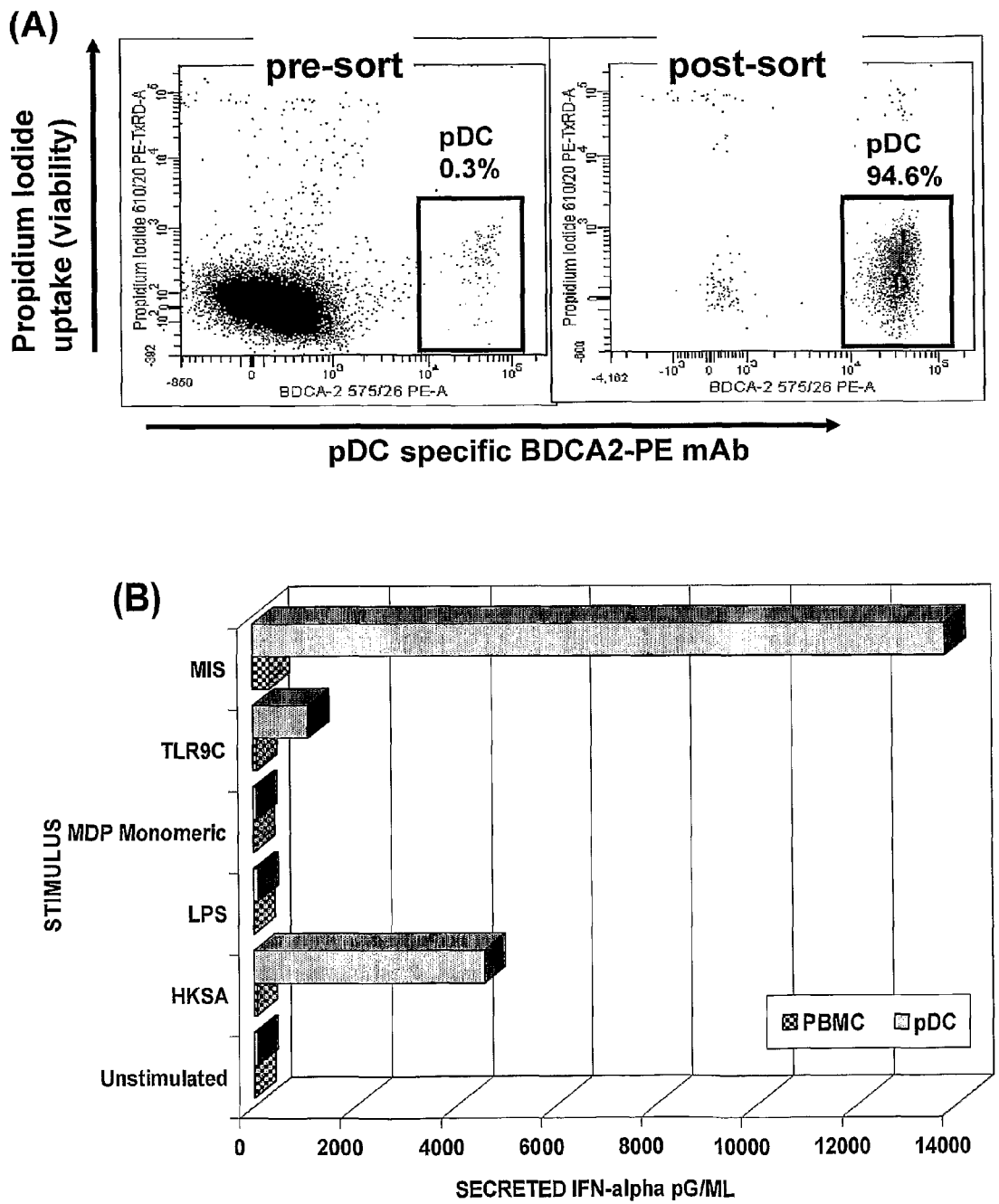
FIG. 3 shows that MDP/DNA-microparticle (MIS) induced IFNα is particularly associated with plasmocytoid dendritic cells.

MDP/DNA-Microparticle (MIS) Induction of IFN-α is Preferentially Mediated by Plasmocytoid Dendritic Cells, which are Known to be the Primary Cellular Sensor for Nucleic Acid Human pDCs were purified from PBMCs using magnetic bead selection of BDCA-2+ cells to high purity and viability (FIG. 3 A). Sorted pDC were cultured at $2.6 \times 10^5$ cells/mL in the presence of recombinant human GM-CSF (200 U/mL) and IL-3 (10 ng/mL) and either with no stimulus, heat-killed *Streptococcus aureus* (HKSA; $1 \times 10^8$ particles/mL), LPS (E coli; 100 ng/mL), monomeric MDP (20 µg/mL), TLR9 type C ligand (CpG ODN M362; 0.1 µm) or MDP/DNA-microparticle (10 µg/mL) for 24 hours. Human PBMC ($10^6$/mL) cultures were initiated in parallel. Supernatants were harvested at 96 hours and assayed for IFN-α content using flow cytometry cytokine bead array methodology. As can be seen in FIG. 3B, enrichment for pDC results in a substantial increase in the amount secreted IFN-α following MDP/DNA-microparticle stimulation as compared to that detected in supernatants from MDP/DNA-microparticle stimulated PBMC.

Example 6

Induction of Monocyte TNFα Production Following 22-Hour Stimulation with MDP/DNA-Microparticle (MIS)

Figure 4:
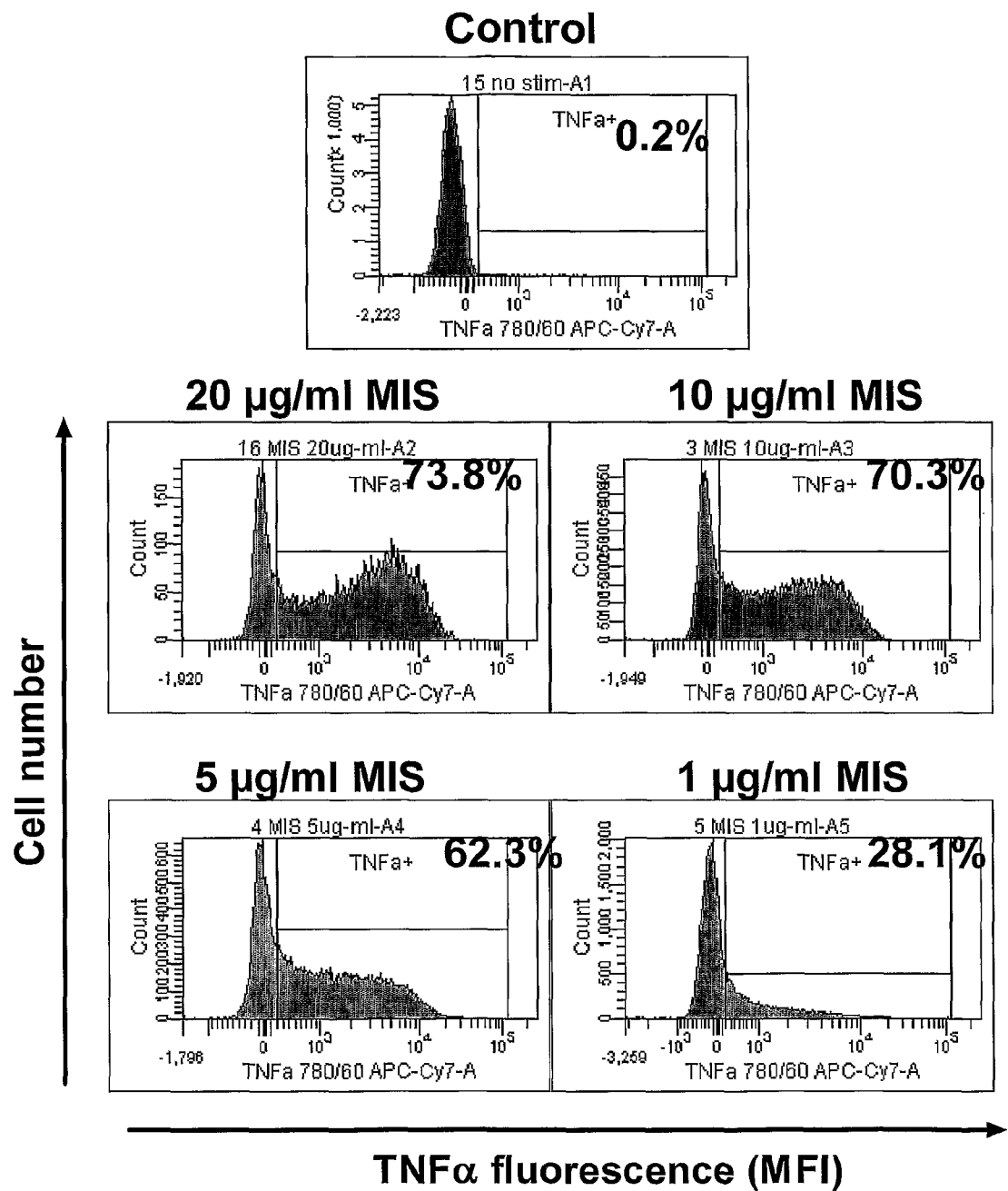
FIG. 4 shows induction of monocyte TNFα production following a 22-hour stimulation with MDP/DNA-microparticle (MIS)

Human PBMC ($10^6$/mL) were cultured with MDP/DNA-microparticle at 20, 10, 5 and 1 µg/mL for 22 hours. A protein transport inhibitor (brefeldin A) was added for the last 6 hours of the culture to enable cytokine accumulation. Cells were labelled with fixable violet live/dead stain (Invitrogen), washed and subsequently fixed/permeabilised using Cytofix/Cytoperm (Becton Dickinson), followed by labelling with anti-TNF-α-APC-Cy7 monoclonal antibody (Becton Dickinson). Viable monocytes were identified based on live/dead dye exclusion combined with FSC-v-high SSC gating. In FIG. 4 the proportion of gated viable monocytes expressing TNF-α at all concentrations of MDP/DNA-microparticle was determined. The largest proportion of viable monocytes expressing TNF-α is 73.8% at 20 µg/mL of MDP/DNA-microparticle.

Example 7

Enhancement of Human PBMC NK Early Activation Antigen Expression Following Stimulation with MDP/DNA-Microparticle (MIS)

Human PBMC ($10^6$/mL) were cultured with MDP/DNA-microparticle at 10, 5 and 1 µg/mL. Known NK cell-activating agent, IL-2 (500 U/mL) served as assay positive control. Following 18 hr culture, PBMC NK activation status was determined by flow cytometric analysis of fluorescent antibody (CD3, CD56 and CD69; Becton Dickinson) labelled cells. Viable NK cells were gated based on propidium iodide⁻

Figure 5:
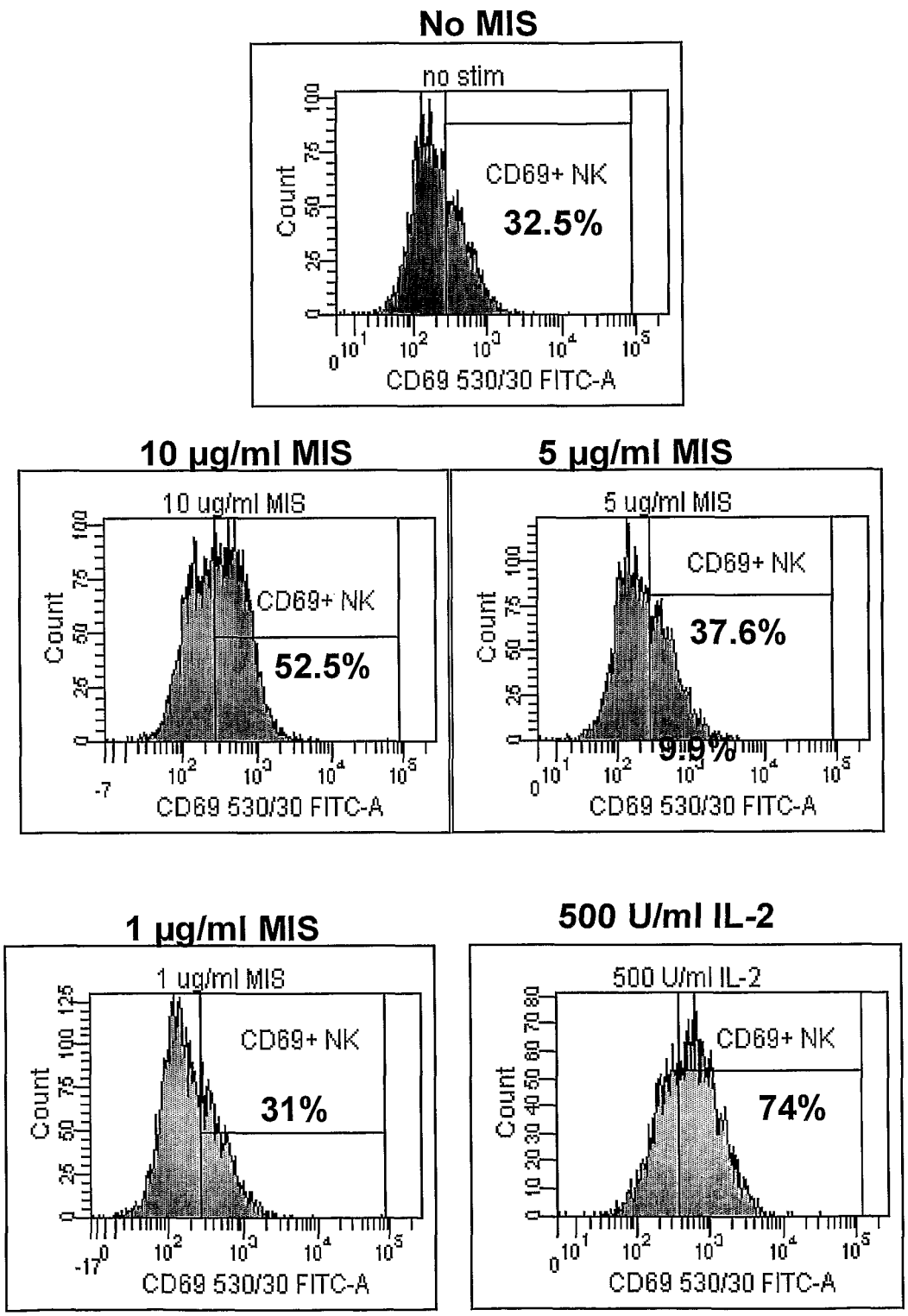
FIG. 5 shows the enhancement of human peripheral blood monocyte (PBMC) NK cell early activation antigen expression following stimulation with MDP/DNA-microparticle (MIS)

CD3⁻CD56⁺ phenotype and CD69 activation antigen expression was determined on the gated population. The region indicating the percentage of NK cells expressing CD69 in the presence or absence of MDP/DNA-microparticle is shown in FIG. 5.

Example 8

IFNγ, GM-CSF, and TNF-α Production by Purified NK and NKT Cells Following a 40-Hour Stimulation with MDP/DNA-Microparticle (MIS)

Figure 6:
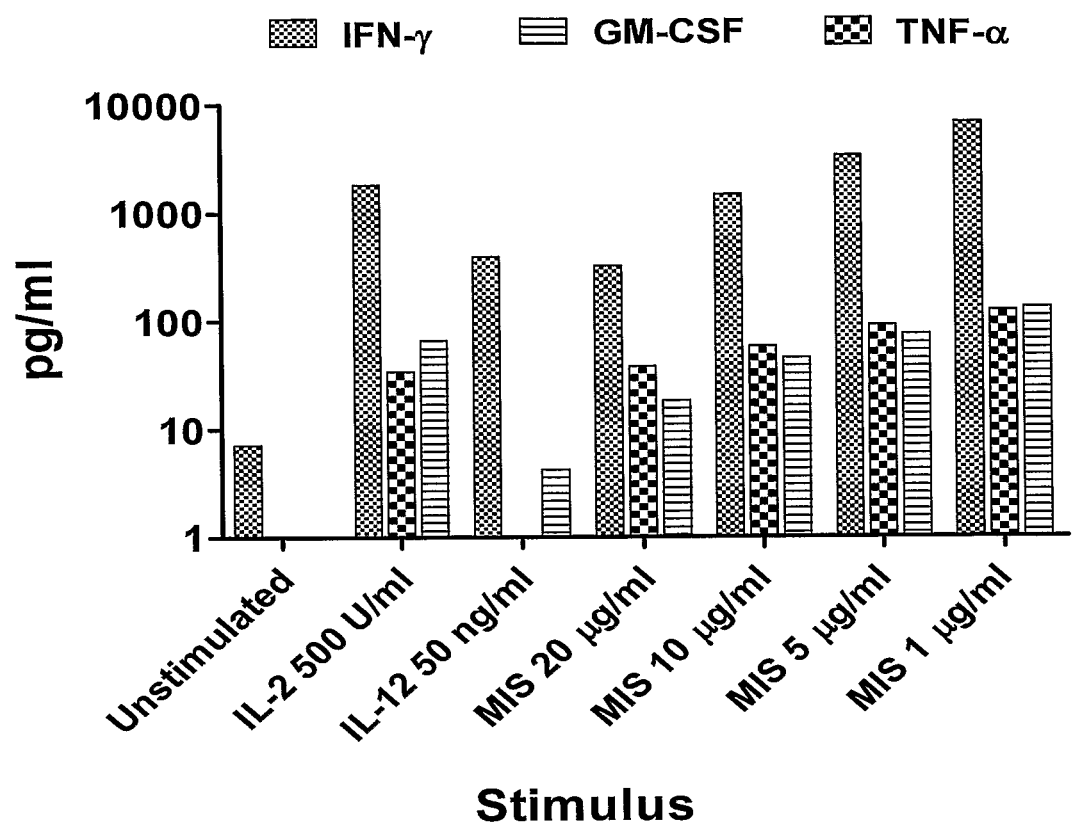
FIG. 6 shows IFNγ, GM-CSF and TNFα production by purified NK and NKT cells following a 40-hour stimulation with MDP/DNA-microparticle (MIS)

Human CD56⁺ cells were purified from whole blood to 99% purity using MACS positive selection beads (Miltenyi), which isolates both NK (CD56⁺CD3⁻) and NKT cells (CD56⁺CD3⁺). Purified cells were then cultured ($7.5 \times 10^5$/mL) with no stimulus, IL-2 (500 U/mL), IL-12 (50 ng/mL), or MDP/DNA-microparticle (20, 10, 5 and 1 µg/mL) for 40 hours. Supernatants were assayed for IFN-γ, TNF-α, and GM-CSF content using flow cytometry cytokine bead array methodology according to manufacturers' standard protocol (Bender MedSystems). As can be seen in FIG. 6, MDP/DNA-microparticle clearly stimulates the production of the antineoplastic cytokines IFNγ and TNFα, as well as GM-CSF which may help the body build an effective immune response to kill cancer cells.

Example 9

Figure 7:
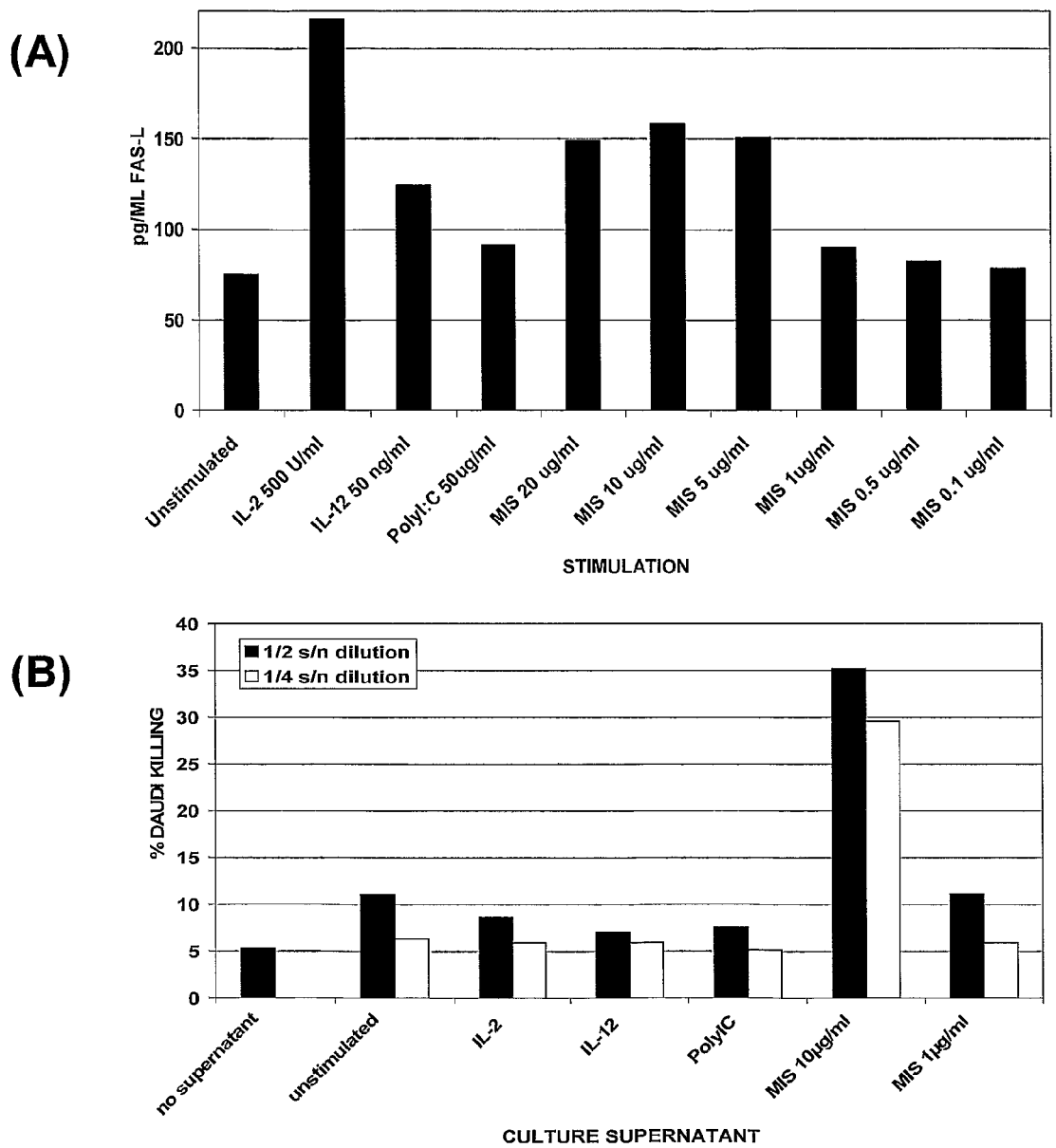
FIG. 7 shows MDP/DNA-microparticle (MIS) stimulation of purified NK and NKT cells resulting in an up-regulation of the release of tumoricidal quantities of FAS-L.

MDP/DNA-Microparticle (MIS) Stimulation of Purified NK and NKT Cells Resulting in an Up-Regulation of the Release of Tumouricidal Quantities of FAS-L Human CD56+ cells were purified from whole blood to 99% purity using MACS positive selection beads, which isolates both NK (CD56⁺CD3⁻) and NKT cells (CD56⁺CD3⁺) according to manufacturers standard protocol (Miltenyi). Purified cells were then cultured at $10^6$/mL with no stimulus, known NK activating agents IL-2 (500 U/mL), IL-12 (50 ng/mL), poly I:C (50 µg/mL) or with MDP/DNA-microparticle (20, 10, 5, 1, 0.5 and 0.1 µg/mL). Following a 20 hour culture, cell-free supernatants were harvested and assayed for soluble FAS-L using flow cytometry bead array methodology according to manufacturers' protocol (Becton Dickinson) as shown in FIG. 7A. MACS purified CD56⁺ cells at $10^6$/mL were then cultured for 69 hours with IL-2 (500 U/mL), IL-12 (50 ng/mL), poly I:C (50 µg/mL) or MDP/DNA-microparticle (10 and 1 µg/mL). Cell-free supernatants were harvested and tested for FAS-mediated cytotoxcity by 4 hour culture of DiD (Invitrogen) fluorescently labelled FAS sensitive Daudi tumour targets with ½ or ¼ diluted supernatants. Daudi cell killing was determined by flow cytometric determination of viability dye (propidium iodide; Invitrogen) uptake (live/dead discrimination) of gated, fluorescent tumour targets. As can be seen in FIG. 7B, the MDP/DNA-microparticle stimulated cell-culture supernatants produced a greater percentage kill of Daudi cells than supernatants from cells stimulated with IL-2, IL-12 or poly I:C.

Example 10

Figure 8:
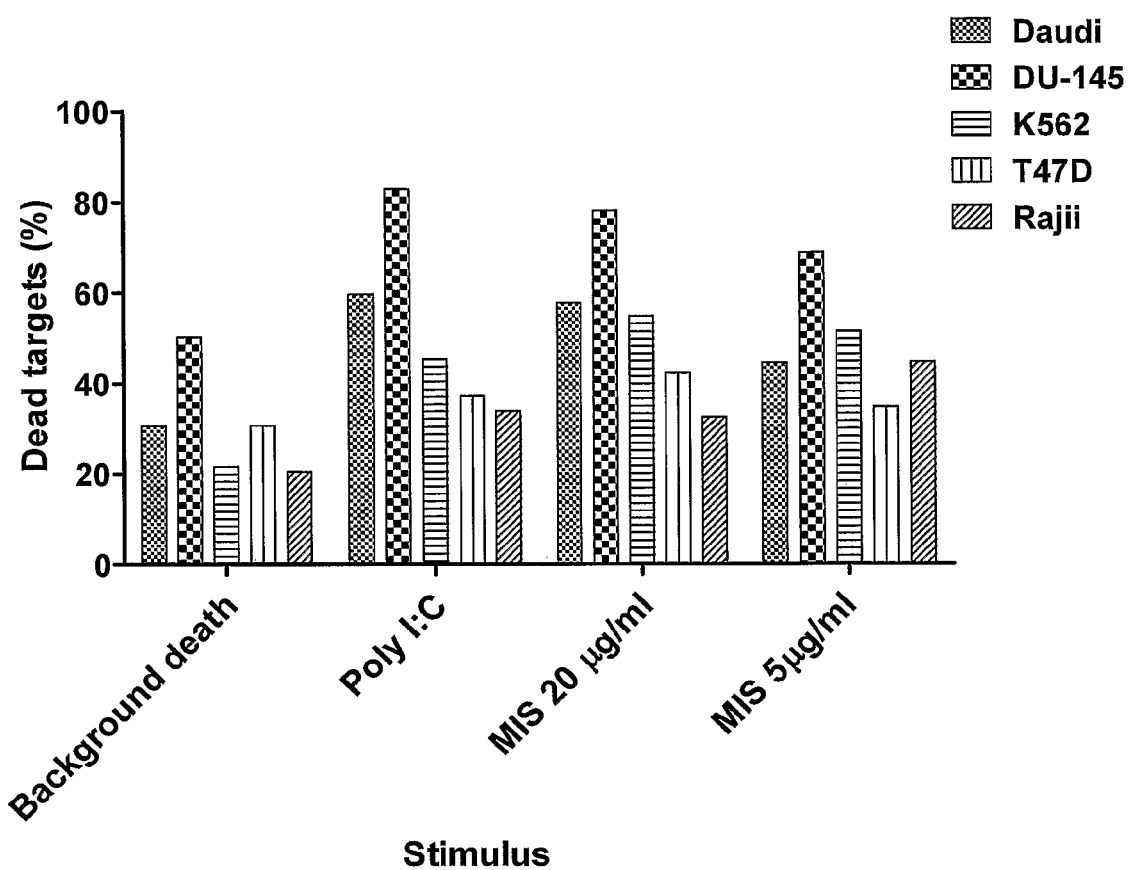
FIG. 8 shows MDP/DNA-microparticle (MIS) mediated enhancement of human PBMC spontaneous killing activity against NK sensitive K562 and DU-145 as well as FAS-L sensitive Daudi and T47D tumour cell targets.

MDP/DNA-Microparticle (MIS) Mediated Enhancement of Human PBMC Spontaneous Killing Activity Against NK Sensitive K562 (Erythroleukemia) and DU-145 (Prostate) as Well as FAS-L Sensitive Daudi (Burkitt's Lymphoma) and T47D (Breast) Tumour Cell Targets Human PBMCs ($10^6$/mL) were cultured with MDP/DNA-microparticle at 20 and 5 µg/mL. Known NK/NKT cell-activating agents, IL-2 (500 U/mL), IL-12 (50 ng/mL) and TLR3 ligand, poly I:C (50 µg/mL) served as assay positive controls. Following a 46 hour culture, activated PBMCs were then washed into fresh medium and tested for cytotoxicity against fluorescently labelled (DiD; Invitrogen) tumour target cells at an effector:target ratio of 100:1. Tumour cell killing was determined after 4 hours by flow cytometric determination of propidium iodide viability dye uptake (live/dead discrimination) of gated, fluorescent tumour targets. From FIG. 8 it can be seen that MDP/DNA-microparticle stimulation enhances human PBMC spontaneous killing activity against NK sensitive K562 (erythroleukemia) and DU-145 (prostate) as well as FAS-L sensitive Daudi (Burkitt's lymphoma) and T47D (breast) tumour cell targets.

Example 11

Enhancement of Purified Human NK Spontaneous Killing Activity Following Stimulation with MDP/DNA-Microparticle (MIS)

Figure 9:
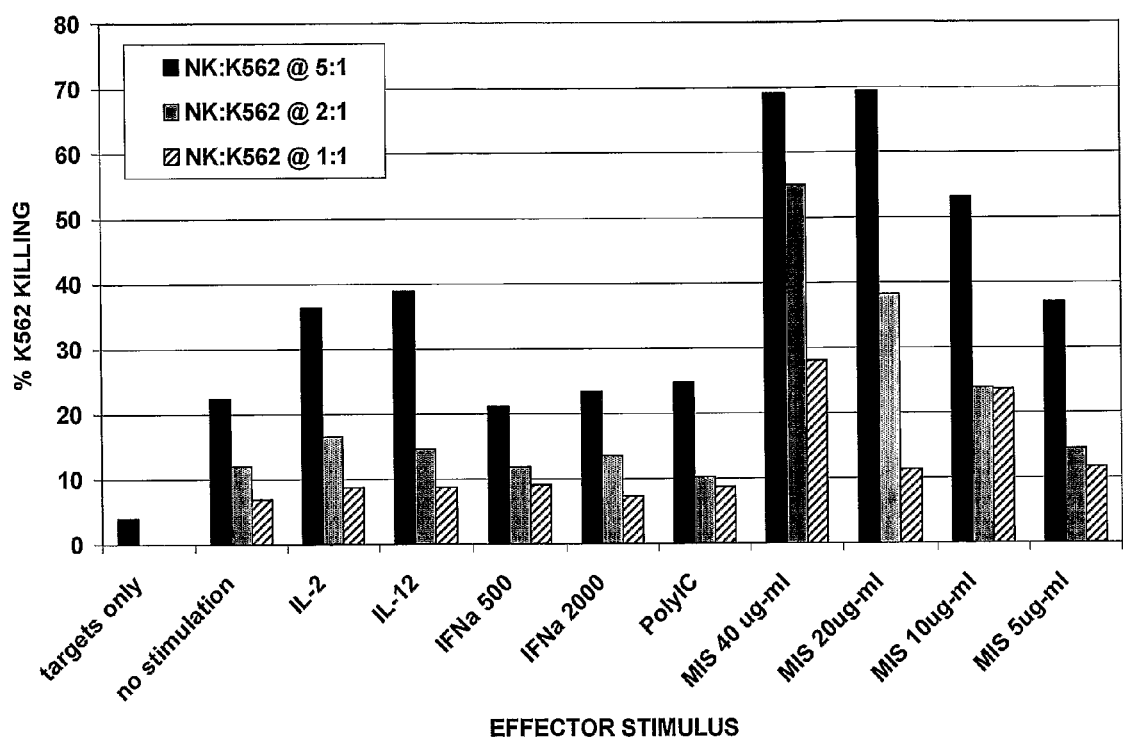
FIG. 9 shows enhancement of purified human NK spontaneous killing activity following stimulation with MDP/DNA-microparticles (MIS)

Human CD56⁺ cells were purified from whole blood to 99% purity using MACS positive selection beads, which isolate both NK (CD56⁺CD3−) and NKT cells (CD56⁺CD3⁺) according to manufacturers standard protocol (Miltenyi). Purified cells were then cultured at $7.5 \times 10^5$/mL with no stimulus, known NK activating agents IL-2 (500 U/mL), IL-12 (50 ng/mL), IFN-α (500 and 2000 U/mL), poly I:C (50 µg/mL) or with MDP/DNA-microparticle (40, 20, 10 and 5 µg/mL). Following a 40 hour culture, stimulated NK cells were washed into fresh medium and tested for cytotoxicity against fluorescently labelled (DiD; Invitrogen) NK sensitive K562 tumour targets at effector:target ratios of 5:1, 2:1 and 1:1. Tumour cell killing was determined after 4 hours by flow cytometric analysis of viability dye uptake (propidium iodide) of gated, fluorescent K562 targets. From FIG. 9 it can be seen that tumour cell killing is greater at all ratios tested when NKcells are stimulated with MDP/DNA-microparticle.

Example 12

Figure 10:
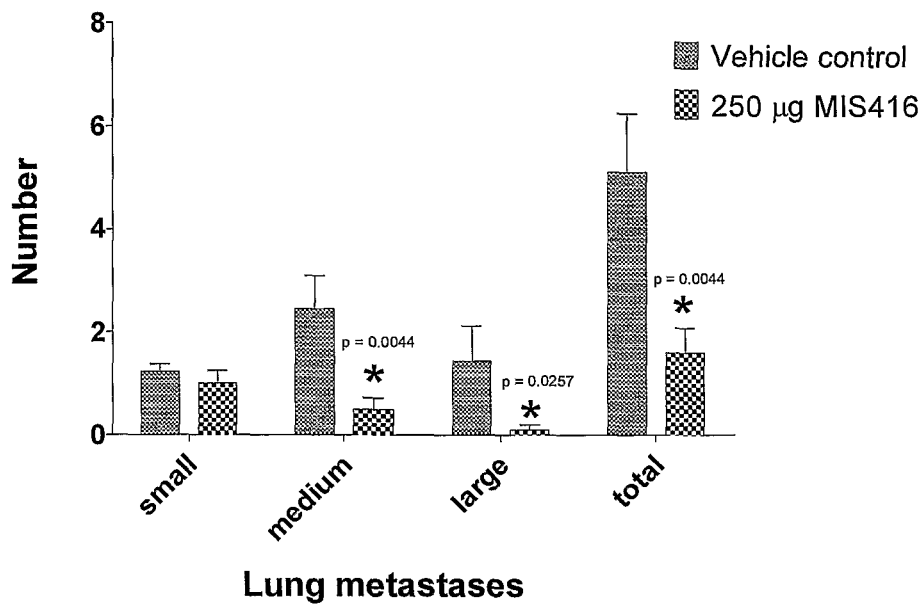
FIG. 10 shows MDP/DNA-microparticle (MIS416) therapy inhibits the formation of lung metastases in animal models of metastatic breast (4T1) and lung (Lewis lung) cancer (* denotes statistical significance relative to control (P<0.0006; unpaired one-tailed t-test and * denotes significance relative to each individual therapy (P<0.0001)
Figure 10:
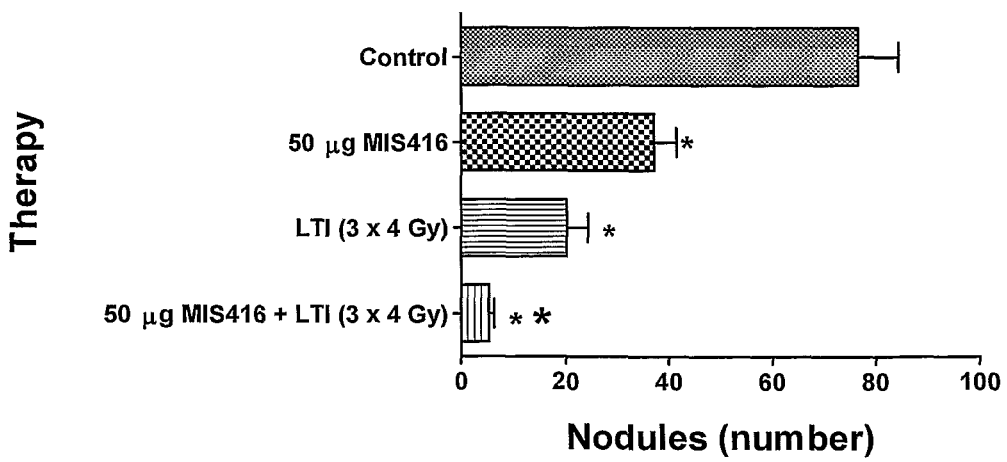

MDP/DNA-Microparticle (MIS416) has Anti-Metastatic Activity as a Stand-Alone Agent or Co-Therapy in Metastatic Breast Cancer and Lewis Lung Carcinoma Models Tumours were established from cultured breast cancer 4T1 cells which were injected in the mammary fat pad (Balb/C; female). At 48 hrs post inoculation, a single 250 µg bolus of MDP/DNA-microparticle was administered via i.v delivery. The numbers of surface lung metastases were determined at study termination (day 23) (FIG. 10A). For analysis of statistical significance * denotes statistical significance relative to control ($P \leq 0.044$; unpaired one-tailed t-test). Female C57B1/6 mice (10 per group) were injected with $10^6$ Lewis Lung carcinoma cells intravenously (FIG. 10B). On day 4 post injection of carcinoma cells, therapy was initiated according the following treatment schedule (i) no treatment (ii) MDP/DNA-microparticle (MIS416) alone, 50 µg (iii) 4Gy lung irradiation on day 5, 6 and 7 (iv) 50 µg MDP/DNA-microparticle (MIS416) plus 4Gy lung irradiation on day 5, 6 and 7. MDP/DNA-microparticle (MIS416) was administered in saline via i.v route. On day 14, lung colonies were removed and assessed for lung colonies. For analysis of statistical significance * denotes statistical significance relative to control ($P < 0.0006$; unpaired one-tailed t-test) and * denotes significance relative to each individual therapy ($P < 0.0001$).

These studies demonstrate that MDP/DNA microparticle therapy inhibits the formation of spontaneous lung metastases that arise from unrelated tumour mass occurring at an anatomically distant site. These studies also demonstrate that MDP/DNA-microparticle therapy is inhibitory for the growth of lung metastases when administered following early, direct establishment of metastases in the lung. Moreover, there is demonstrable synergy between local radiotherapy and MDP/DNA-microparticle co-therapy for inhibition of lung metastases growth. This indicates that a combinatorial anti-neoplastic regimen that includes innate immunostimulation can lead to an improved therapeutic outcome.

Example 13

Figure 11:
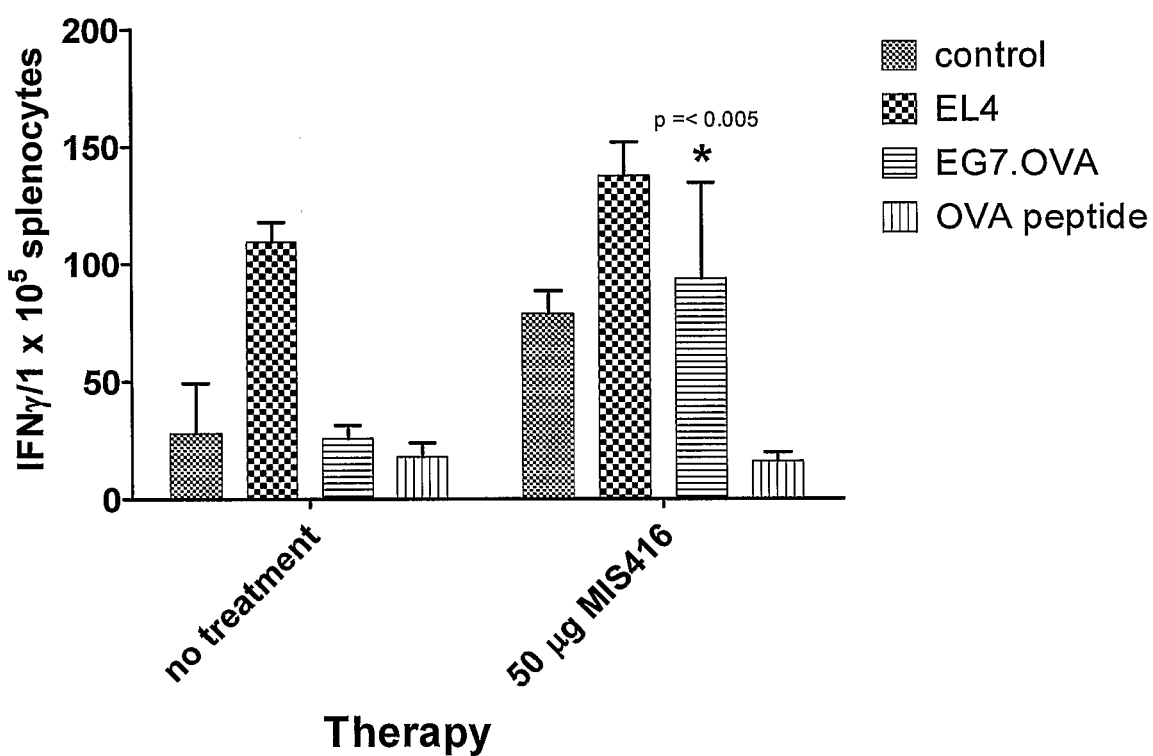
FIG. 11 shows MDP/DNA-microparticle (MIS416) therapeutic vaccination of animals harbouring tumours which overexpress a tumour associated antigen leads to the induction of adaptive Th1 cellular tumour antigen-specific immune responses.

MDP/DNA-Microparticle (MIS416) Therapy Induces a Cellular Immune Response Towards Endogenous Tumour Associated Antigen (OVA) in a B16-Ova Therapeutic Vaccine Model Syngeneic C57/B16 mice were implanted with B16-OVA cells ($1 \times 10^6$ per mouse) and tumours were allowed to grow until 4-5 mm diameter. MDP/DNA-microparticle was administered on day 8 by i.v delivery of a single 50 μg bolus. On day 20 following therapy, spleens were excised and antigen restimulation assays were performed against EL4-MART and B16-OVA tumour cells as well as soluble OVA peptide (FIG. 11). ELISPOT quantitation of IFN-γ secreting cells was performed as a measure of IFN-γ expressing cytotoxic CD8$^+$T cells. OVA tetramer binding assays have confirmed the increased frequency of splenic OVA specific CD8$^+$T cells in this model. MDP/DNA-microparticle therapy significantly increased the frequency of IFN-γ OVA-specific T cells relative to non-treated or irrelevant controls (* denotes statistical significance relative to control (P<0.005; unpaired one-tailed t-test). These studies demonstrate that MDP/DNA-microparticle therapy has immunostimulatory, adjuvant properties that support the induction of adaptive immune responses directed preferentially towards a tumour associated antigen. This is desirable, since these types of responses lead to the development of adaptive, protective immunity towards autologous tumours preventing the re-occurrence of primary and/or metastatic disease.

Example 14

Figure 12:
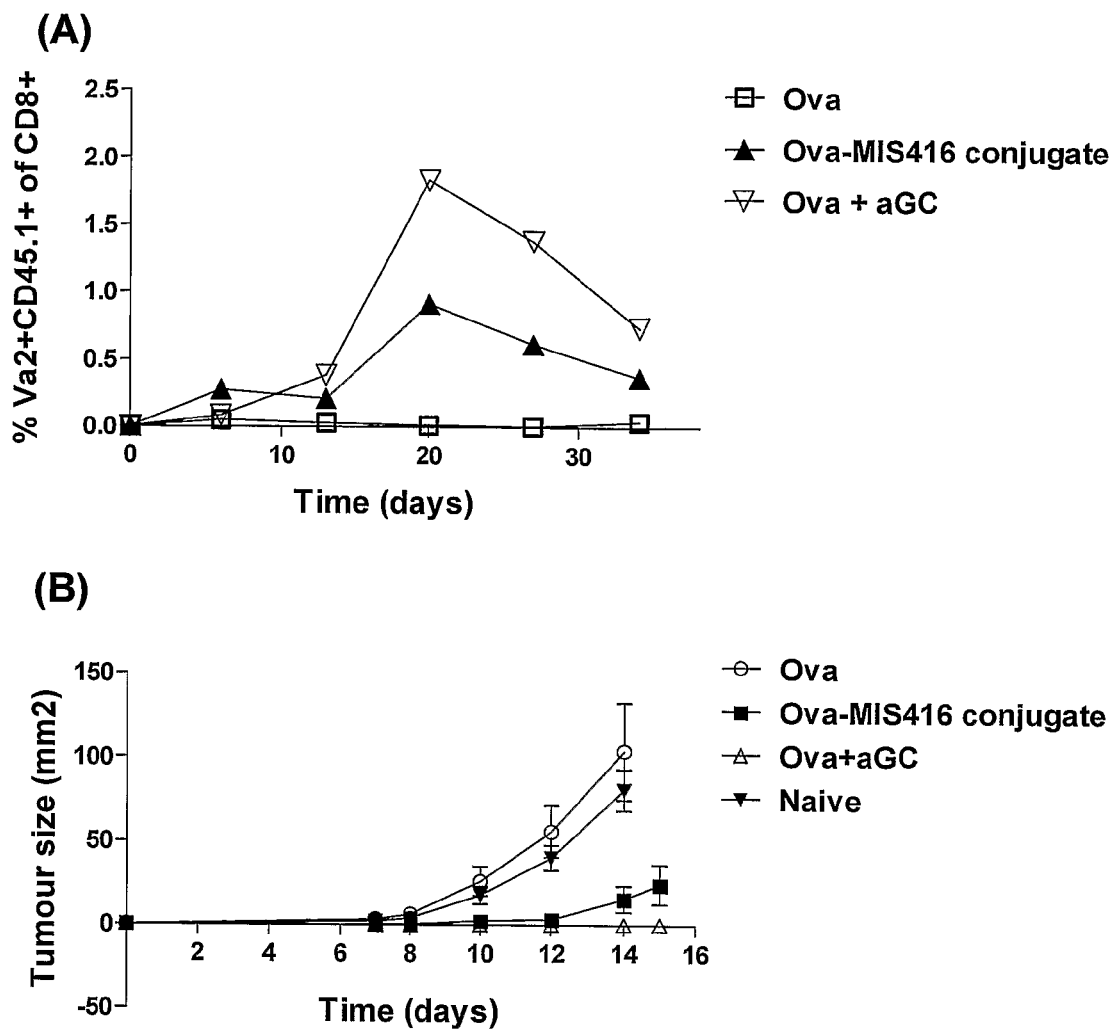
FIG. 12 shows prophylactic immunization with MDP/DNA-microparticle-OVA tumour antigen immunoconjugate (OVA-MIS416 conjugate) induces peripheral expansion of OVA-specific CD8$^+$T cells and induction of protective immunity towards subsequent OVA tumour challenge.

Vaccination with OVA-MDP/DNA-Microparticle (MIS416) Immunoconjugates Induces Peripheral Expansion of Adoptively Transfered OT-1 CD8+ Cells and Induction of Anti-Tumour Immunity in a Prophylactic Tumour Vaccine Model (A) Syngeneic purified CD8$^+$ OT-I cells ($10^3$) were adoptively transferred to groups of mice (C57/B16; n=10) via i.v delivery followed by i.v immunization with either 25 μg OVA, 25 μg OVA-MDP/DNA-microparticle (MIS416) immunoconjugate or 25 μg OVA mixed with 200 ng α-galactoceramide (positive control for i.v immunization for Th1 responses). Peripheral blood was sampled at various time points up to day 35 post immunization. The expansion of OT-I cells was determined using flow cytometric analysis for T cells with a CD8$^+$ CD45.1+Vα2+ phenotype (OT-I specific) (FIG. 12A). On day 36 post immunizations, $10^6$ B16-OVA tumour cells were injected s.c. and tumour growth was monitored (FIG. 12B). These results demonstrate that pre-treatment with MDP/DNA-microparticle-tumour antigen immunoconjugates induces protective Th1 type immune responses. These responses are associated with tumour rejection.

Example 15

Figure 13:
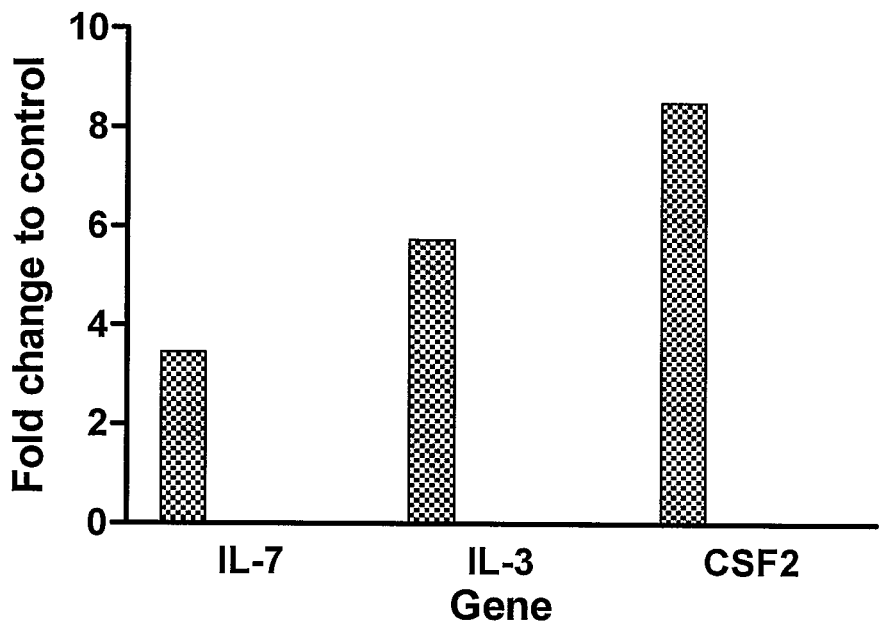
FIG. 13 shows that MDP/DNA-microparticle (MIS416) stimulation of PBMC results in the production of hematopoietic factors IL-3, GMCSF and IL-7.
Figure 13:
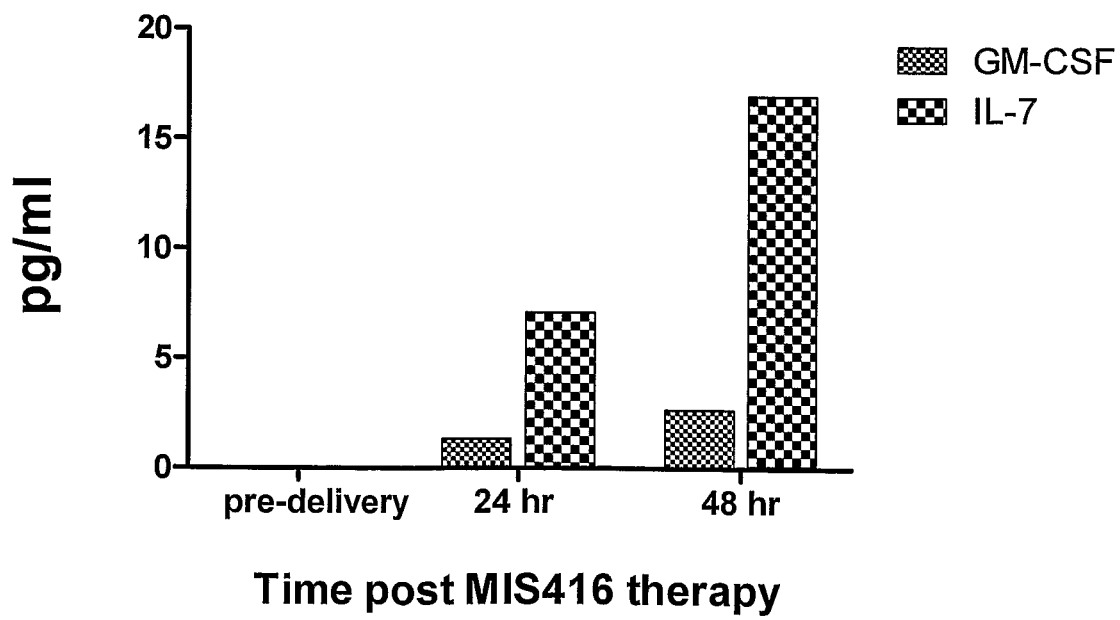

Treatment with MDP/DNA-Microparticle (MIS416) In Vitro and In Vivo Leads to the Production of Growth Factors that are Central to Immune Replenishment and Functional Reconstitution Healthy donor PBMC and incubated for 6 hours at 37 degree centigrade with 5 μg/mL MDP/DNA-microparticle. Non-stimulated cell cultures were established as a control. Whole RNA from the PBMC was extracted using ROCHE RNA extraction kit and cDNA was synthesized also using ROCHE cDNA synthesis kit. This cDNA was put with primers coated in individual wells in a 96 well format. Real time quantitative PCR was conducted for a range of human genes and the fluorescence was read. The fold changes calculated for each gene by determining the differential expression between an un-stimulate and a stimulated fraction. An increased fold change is reflective of an upregulation. The upregulation of IL-3, IL-7 and CSF2 (GMCSF) was detected (FIG. 13A). Peripheral blood serum was harvested at 24 and 48 hours following i.v administration of a single 500 μg bolus of MDP/DNA-microparticle. The concentration of IL7 and GMCSF was determined using flow cytometry cytokine bead array methodology carried out according to manufacturers' standard protocol (Becton Dickinson) (FIG. 13B).

Although the invention has been described with reference to certain preferred embodiments and examples it will be understood that variations in keeping with the spirit of the invention and the disclosure provided herein are also contemplated.

The claims defining the invention are as follows:

1. A method of treating neoplastic disease comprising administering to a subject requiring such treatment an effective amount of microparticles comprising muramyl dipeptide (MDP), wherein the dipeptide moiety of the MDP is amino-linked L-alanine-D-isoglutamine and the MDP is crosslinked with bacterial DNA, and wherein the size of the microparticles is predominantly in the range of 0.5-3 microns.

2. A method according to claim 1, wherein the microparticle is combined with at least one immunostimulatory ligand, bound to or within the microparticle, which is capable of stimulating immune cell subsets effective in inhibiting tumour cell growth and/or proliferation, or effective in tumour cell damage and/or destruction.

3. A method according to claim 2, wherein the immunostimulatory ligand is selected from one or more molecular pattern recognition receptor families or is an immunostimulatory glycolipid antigen.

4. A method according to claim 3, wherein the molecular pattern recognition receptor ligand is selected from one or more of TLR1,2,3,4,5,6,7,8,9,10, NOD-1 and NOD-2 and the glycolipid antigen is α-GalCer or an analogue thereof.

5. A method according to claim 2, wherein the immunostimulatory ligand is cross-linked on the surface or within the microparticle.

6. A method according to claim 1, wherein the microparticle has an overlapping immunostimulatory effect with that induced by interleukin-2 (IL-2).

7. A method according to claim 1, wherein the microparticle stimulates the production of anti-neoplastic cytokines selected from interferon-alpha (IFNα), interferon-gamma (IFNγ), granulocyte-macrophage colony-stimulating factor (GM-CSF), interleukin 12 (IL-12) and TNFα.

8. A method according to claim 1, wherein the neoplastic disease is selected from carcinoma, sarcoma, myeloma, leukaemia, lymphoma or a mixed-type.

9. A method according to claim 1, wherein, the neoplastic disease is selected from fibrosarcoma, myxosarcoma, liposarcoma, chondrosarcoma, osteosarcoma, chordoma, malignant fibrous histiocytoma, hemangiosarcoma, angiosarcoma, lymphangiosarcoma, mesothelioma, acute myelogenous leukaemia, acute lymphoblastic leukaemia, chronic myelogenous leukaemia, chronic lymphoblastic leukaemia, plasmacytoma, multiple myeloma, Hodgkin lymphoma and non-Hodgkin lymphoma, rhabdomyosarcoma, leiomyosarcoma, squamous cell carcinoma, epidermoid carcinoma, adenocarcinoma, hepatocellular carcinoma, renal cell carcinoma, hypernephroma, cholangiocarcinoma, transitional cell carcinoma, choriocarcinoma, seminoma, embryonal cell carcinoma, glioma, anaplastic glioblastoma multiforme, neuroblastoma, medulloblastoma, malignant meningioma, malignant meningioma, malignant schwannoma, neurofibrosarcoma, parathyroid carcinoma, medullary carcinoma of thyroid, bronchial carcinoid, oat cell carcinoma, malignant pheochromocytoma, islet cell carcinoma, malignant carcinoid, malignant paraganglioma, melanoma, malignant schwannoma, merkel cell neoplasm, cystosarcoma phylloides, Wilms' tumour, dysgerminoma, retinoblastoma and teratocarcinoma.

10. A method according to claim 1, further comprising administering one or more other anti-neoplastic agents for the treatment of neoplastic disease.

11. A method according to claim 10, wherein the other anti-neoplastic agent is selected from alkylating agents, for example, cisplatin, carboplatin, busulfan, chlorambucil and carmustine; antimetabolites, for example, azathioprine and mercaptopurine; alkaloids, for example, vincristine, vinblastine, vinorelbine, vindesine, podophyllotoxin and taxol; type I or type II topoisomerase inhibitors; antibiotics, for example, dactinomycin, bleomycin and doxorubicin or hormones and cytokines, for example, IL-2, IFNγ, GM-CSF, TNFα or IFN-α.

12. A method according to claim 1, wherein the subject has metastases.

13. A method according to claim 1, wherein the microparticles stimulate release of cytokines, chemokines and cytotoxic proteins in the subject.

14. A method according to claim 13, wherein the cytokines, chemokines and cytotoxic proteins are selected from IL-2, IFNγ, IFNα, GM-CSF, TNFα, TRAIL and FasL.

15. A method according to claim 14, wherein the microparticle stimulates secretion of IFNα from peripheral blood plasmocytoid dendritic cells (pDCs).

16. A method according to claim 14, wherein the microparticle stimulates secretion of TNFα from monocytes.

17. A method according to claim 1, wherein the microparticle is in combination with one or more tumour-associated antigens, bound to or within the microparticle, capable of stimulating a tumour specific immune response.

18. A method according to claim 17, wherein the tumour-associated antigen is selected from autologous tumour cells, CEA, CA19-9, CA125, EP-CAM, her-2/neu, melanoma antigen and GM2.

19. A method according to claim 13, wherein the microparticle is in combination with one or more tumour-associated antigens, bound to or within the microparticle, capable of stimulating a tumour specific immune response.

20. A method according to claim 19, wherein the tumour-associated antigen is selected from autologous tumour cells, CEA, CA19-9, CA125, EP-CAM, her-2/neu, melanoma antigen and GM2.

* * * * *